United States Patent
Kang et al.

(10) Patent No.: US 9,649,081 B2
(45) Date of Patent: May 16, 2017

(54) X-RAY IMAGE APPARATUS AND CONTROL METHOD FOR THE SAME

(71) Applicant: SAMSUNG ELECTRONICS CO., LTD., Suwon-si (KR)

(72) Inventors: Dong Goo Kang, Hwaseong-si (KR); Seok Min Han, Seongnam-si (KR); Young Hun Sung, Hwaseong-si (KR); Jae Mock Yi, Hwaseong-si (KR); Jae Hak Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 152 days.

(21) Appl. No.: 14/501,344

(22) Filed: Sep. 30, 2014

(65) Prior Publication Data

US 2015/0092919 A1    Apr. 2, 2015

(30) Foreign Application Priority Data

Oct. 1, 2013    (KR) .................. 10-2013-0117160

(51) Int. Cl.
*A61B 6/00* (2006.01)

(52) U.S. Cl.
CPC .............. *A61B 6/482* (2013.01); *A61B 6/405* (2013.01); *A61B 6/4241* (2013.01); *A61B 6/481* (2013.01);
(Continued)

(58) Field of Classification Search
CPC ................................. A61B 6/482; A61B 6/405
See application file for complete search history.

(56) References Cited

U.S. PATENT DOCUMENTS

| 6,097,788 A * | 8/2000 | Berenstein ............... H05G 1/70 378/62 |
| 2011/0235885 A1 | 9/2011 | Rauch et al. |
| 2011/0235889 A1 * | 9/2011 | Spahn .................. A61B 6/4441 382/132 |

FOREIGN PATENT DOCUMENTS

| JP | 2009-178493 A | 8/2009 |
| JP | 2011-206240 A | 10/2011 |

(Continued)

*Primary Examiner* — Hoon Song
(74) *Attorney, Agent, or Firm* — Sughrue Mion, PLLC

(57) ABSTRACT

Disclosed herein are an X-ray image apparatus and a control method for the same. The X-ray image apparatus includes an X-ray generator configured to sequentially irradiate an object with a plurality of X-rays of mutually different energy bands, an X-ray detector configured to acquire a plurality of pieces of X-ray data corresponding to the plurality of mutually different energy bands by detecting X-rays transmitted through the object, an image processor configured to convert the acquired plurality of pieces of X-ray data into a plurality of X-ray images and separate blood vessel X-ray images of the object from the plurality of X-ray images, and a controller configured to control operations of the X-ray generator so that the sequentially irradiated plurality of X-rays of the mutually different energy bands are repeatedly irradiated for fixed cycles. The X-ray generator may be configured to sequentially irradiate the object with the plurality of X-rays for a first time interval in the fixed cycles, and the first time interval may be different from a second time interval that is a time interval between a time point at which a final X-ray of a single cycle among the fixed cycles is irradiated and a time point at which a first X-ray of the following cycle among the fixed cycles is irradiated.

17 Claims, 19 Drawing Sheets

(52) U.S. Cl.
CPC .............. *A61B 6/502* (2013.01); *A61B 6/504* (2013.01); *A61B 6/5235* (2013.01); *A61B 6/54* (2013.01); *A61B 6/4441* (2013.01)

(56) References Cited

FOREIGN PATENT DOCUMENTS

| KR | 10-2007-0095079 A | 9/2007 |
| KR | 10-2012-0039410 A | 4/2012 |

* cited by examiner

X-RAY IMAGE APPARATUS AND CONTROL METHOD FOR THE SAME

CROSS-REFERENCE TO RELATED APPLICATION

This application claims the benefit of Korean Patent Application No. 10-2013-0117160, filed on Oct. 1, 2013 in the Korean Intellectual Property Office, the disclosure of which is incorporated herein by reference in its entirety.

BACKGROUND

1. Field

Exemplary embodiments of the present disclosure relate to an X-ray image apparatus that generates X-ray images by transmitting X-rays through an object and a control method for the same.

2. Description of the Related Art

An X-ray image apparatus is an apparatus which irradiates an object with X-rays and acquires internal images of the object using the X-rays transmitted through the object. Since permeability of the X-rays is different according to characteristics of a material constituting the object, an internal structure of the object may be imaged by detecting an intensity or strength of the X-rays transmitted through the object.

Specifically, when an X-ray generation unit generates X-rays and irradiates an object with the generated X-rays, an X-ray detection unit detects the X-rays transmitted through the object and converts the detected X-rays into electric signals. Since the conversion to the electric signals is performed for each pixel, a single X-ray image may be obtained by combining electric signals corresponding to each pixel.

As a part of the X-ray image, a digital subtraction angiography image is widely utilized. In a method of extracting blood vessels from an existing contrast image, there are problems that quality of the image is significantly deteriorated and a severe change in illumination occurs when performing radiography. However, in digital subtraction angiography technology, a blood vessel area can be prominently expressed in an image in which noise and contrast are severe to thereby control problems occurring in the related art, thereby increasing utilization frequency of digital subtraction angiography technology.

SUMMARY

Therefore, it is an aspect of the exemplary embodiments to provide an X-ray image apparatus which may reduce an error that can occur from a degree of spread of a contrast medium over time by non-uniformly generating a plurality of X-rays of mutually different energy bands, and a control method for the same.

Additional aspects of the exemplary embodiments will be set forth in part in the description which follows and, in part, will be obvious from the description, or may be learned by practice of the exemplary embodiments.

In accordance with an aspect of an exemplary embodiment, there is provided an X-ray image apparatus including: an X-ray generator configured to sequentially irradiate an object with a plurality of X-rays of mutually different energy bands; an X-ray detector configured to acquire a plurality of pieces of X-ray data corresponding to the plurality of mutually different energy bands by detecting X-rays transmitted through the object; an image processor configured to convert the acquired plurality of pieces of X-ray data into a plurality of X-ray images and separate blood vessel X-ray images of the object from the plurality of X-ray images; and a controller configured to control operations of the X-ray generator so that the sequentially irradiated plurality of X-rays of the mutually different energy bands are repeatedly irradiated for fixed cycles. The X-ray generator may sequentially irradiate the object with the plurality of X-rays for a first time interval in the fixed cycles, and the first time interval may be different from a second time interval that is a time interval between a time point at which a final X-ray of a single cycle among the fixed cycles is irradiated and a time point at which a first X-ray of the following cycle among the fixed cycles is irradiated.

In accordance with another aspect of an exemplary embodiment, there is provided a control method for an X-ray image apparatus including: sequentially irradiating an object with a plurality of X-rays of mutually different energy bands; acquiring a plurality of pieces of X-ray data corresponding to the plurality of mutually different energy bands by detecting X-rays transmitted through the object; converting the acquired plurality of pieces of X-ray data into a plurality of X-ray images and separating blood vessel X-ray images of the object from the plurality of X-ray images; and controlling the sequentially irradiating of the object to be repeated for fixed cycles. The sequentially irradiating of the object may include sequentially irradiating the object with the plurality of X-rays for a first time interval in the fixed cycles, and the first time interval may be different from a second time interval that is a time interval between a time point at which a final X-ray of a single cycle among the fixed cycles is irradiated and a time point at which a first X-ray of the following cycle among the fixed cycles is irradiated.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which.

DETAILED DESCRIPTION

Figure 1:
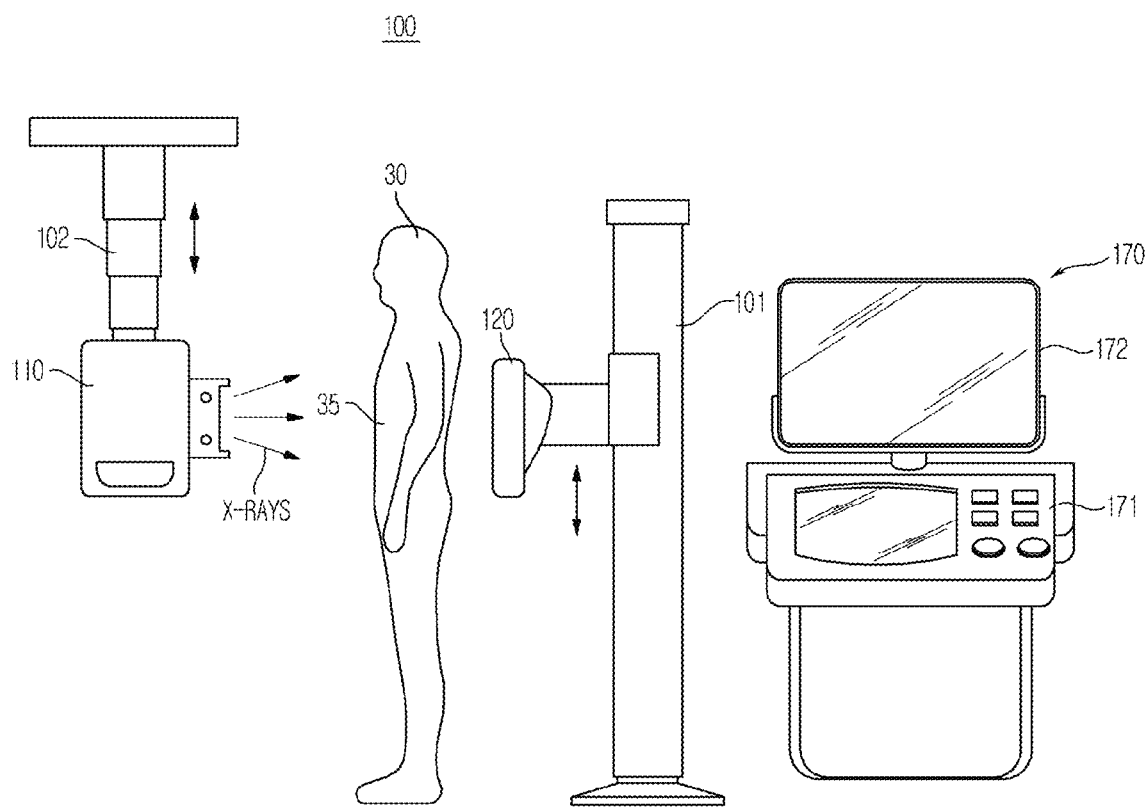
FIG. 1 illustrates an appearance of a general X-ray image apparatus.

Reference will now be made in detail to the exemplary embodiments, examples of which are illustrated in the accompanying drawings, wherein like reference numerals refer to like elements throughout.

A structure or an imaging method of an X-ray image apparatus may vary in accordance with an imaging region, a type of an X-ray image, or an imaging purpose. Specifically, a general X-ray image apparatus for imaging a chest, arms, legs, etc., an X-ray image apparatus using mammography, an X-ray image apparatus using fluoroscopy, an X-ray image apparatus using angiography or cardiovascular angiography, an X-ray image apparatus using computed tomography, and the like are used, and the X-ray image apparatus in accordance with an exemplary embodiment may be any one of the above-described X-ray image apparatuses or a combination of at least two thereof.

FIG. 1 illustrates an appearance of a general X-ray image apparatus.

Referring to FIG. 1, a general X-ray image apparatus 100 may include an X-ray generation unit 110 (e.g., X-ray generator), an X-ray detection unit 120 (e.g., X-ray detector), and a host device 170.

The X-ray generation unit 110 may generate X-rays in order to obtain an X-ray image for an object 35 and irradiate a subject 30 with the generated X-rays.

Here, the subject 30 may be a living body of a human being or animal, but the subject in accordance with an exemplary embodiment is not limited thereto. That is, anything can be the subject as long as its internal structure can be imaged by the X-ray image apparatus 100.

In addition, the object 35 refers to a portion to be diagnosed inside the subject 30 using the X-ray image apparatus 100, that is, a radiography part. Thus, as shown in FIG. 1, when the subject 30 is placed on a table, the object 35 may be a head, a chest, arms, legs, or the like.

The X-ray generation unit 110 may be mounted on a ceiling so as to be movable in the longitudinal direction of the table. The X-ray generation unit 110 is moved in the longitudinal direction of the table, whereby a position of the X-ray generation unit 110 may correspond to a position of the object 35.

The X-ray detection unit 120 may be disposed on the opposite side of the X-ray generation unit 110 with the object 35 interposed therebetween, thereby detecting X-rays which are irradiated from the X-ray generation unit 110 and transmitted through the object 35. In addition, the X-ray detection unit 120 may convert the detected X-rays into electric signals.

The X-ray detection unit 120 may be mounted inside the table so as to be movable in the longitudinal direction of the table. In the same manner as in the X-ray generation unit 110, a position of the X-ray detection unit 120 may be moved so as to correspond to the position of the object 35 in the longitudinal direction of the table.

Unlike FIG. 1, the subject 30 may be placed on the table, the X-ray generation unit 110 may be mounted on the ceiling so as to be movable in the longitudinal direction of the table, and the X-ray detection unit 120 may be mounted inside the table so as to be movable in the longitudinal direction of the table.

The host device 170 may include an input unit 171 that receives instructions from a user and a display unit 172 (e.g., display) that displays X-ray images, and may provide a user interface. Here, the user is a person who performs diagnosis on the object 35 and may be a medical staff such as a doctor, a radiologist, a nurse, and the like, but is not limited thereto. That is, anyone using the X-ray image apparatus 100 may be the user.

The input unit 171 may include at least one of a switch, a keyboard, a track ball, and a touch screen, but is not limited thereto.

A cathode ray tube (CRT), a liquid crystal display (LCD), a light emitting diode (LED), or the like may be applied as the display unit 172, but the display unit 172 is not limited thereto.

Figure 2:
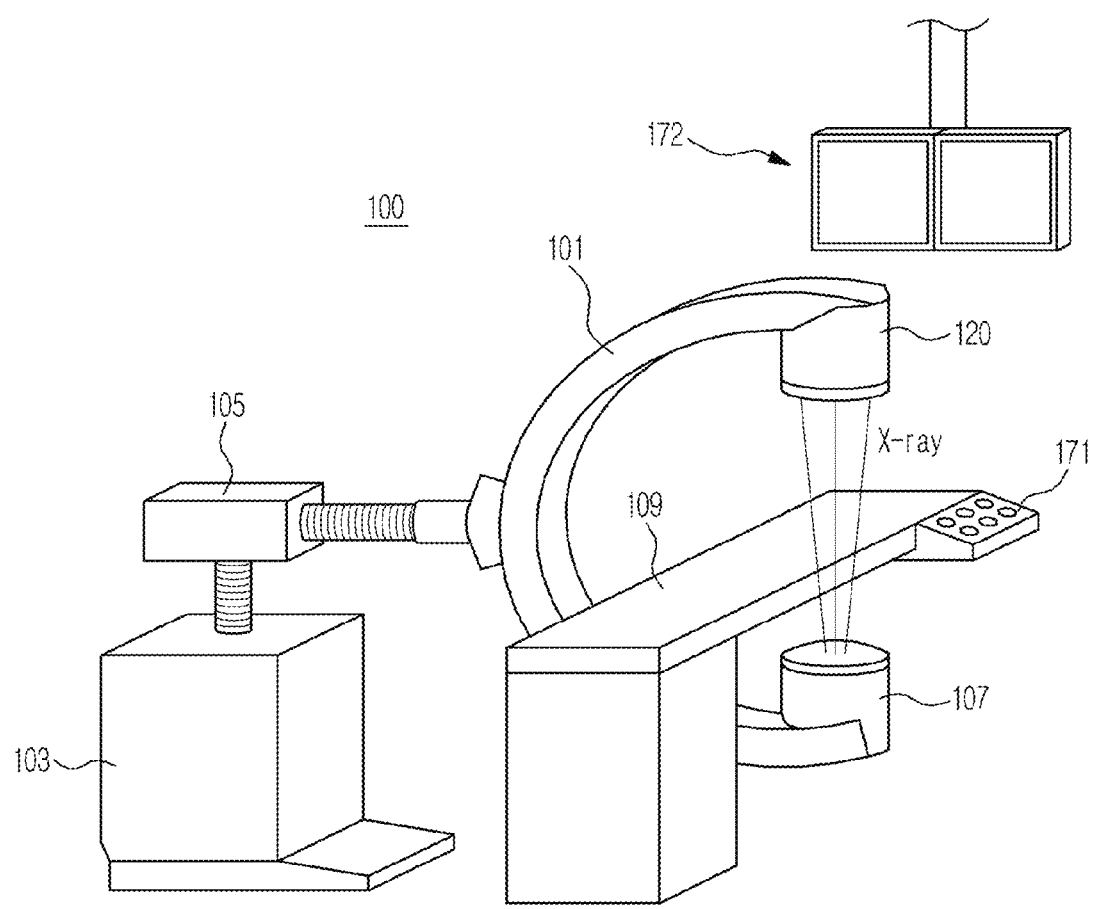
FIG. 2 illustrates an appearance of an X-ray image apparatus for angiography.

FIG. 2 illustrates an appearance of an X-ray image apparatus for angiography.

The X-ray image apparatus 100 may have a C-arm structure as shown in FIG. 2. An X-ray generation assembly 107 and the X-ray detection unit 120 may be respectively mounted in both ends of a C-shaped arm 101 (C-arm). The C-arm 101 may be connected to a main body 103 through a connection shaft 105 to be rotatable in an orbital direction.

The X-ray generation unit 110, a collimator, and a filtering unit are provided inside the X-ray generation assembly 107. A patient table 109 is located between the X-ray generation assembly 107 and the X-ray detection unit 120. When an object is positioned on the patient table 109, the X-ray generation unit 110 irradiates the object with X-rays, and the X-ray detection unit 120 acquires an X-ray image of the object by detecting the irradiated X-rays.

The X-ray image apparatus 100 for angiography may perform radiography in accordance with various imaging modes, and obtain real-time moving images for the object, and therefore a user may perform a treatment or diagnosis while viewing the display unit 172 which includes a plurality of screens and displays various images required for treatment or diagnosis.

The user may input required information through the input unit 171 provided in the X-ray image apparatus 100. For example, the user may input a cycle through the input unit so that the X-ray generation unit which will be described later can repeatedly irradiate X-rays. The input cycle may be transmitted to a control unit 140 (e.g., controller), and the control unit 140 may control the X-ray generation unit 110 in accordance with the input cycle.

Figure 3:
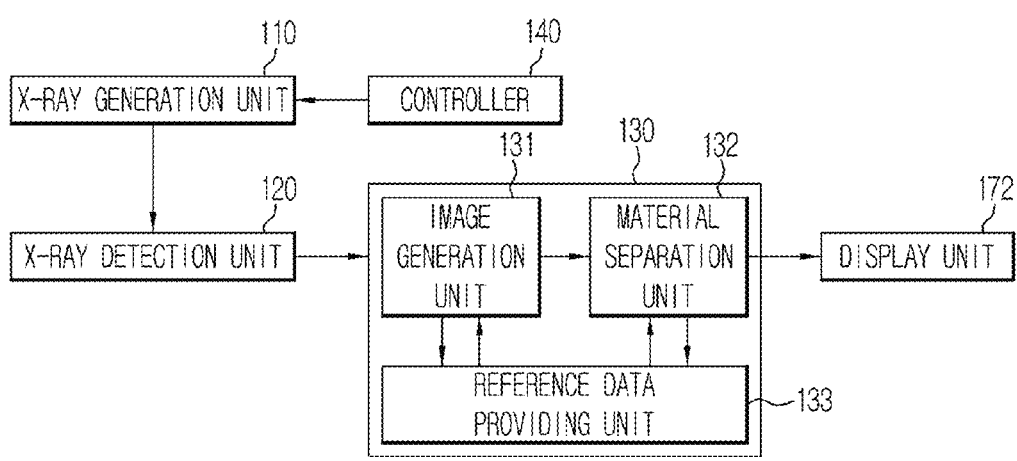
FIG. 3 is a control block diagram illustrating an X-ray image apparatus in accordance with an exemplary embodiment.

FIG. 3 is a control block diagram illustrating an X-ray image apparatus 100 in accordance with an exemplary embodiment.

Referring to FIG. 3, the X-ray image apparatus 100 in accordance with an exemplary embodiment may include the X-ray generation unit 110 that generates X-rays and irradiates the object 35 with the generated X-rays, the X-ray detection unit 120 that acquires X-ray data by detecting the X-rays transmitted through the object 35, and an image processing unit 130 (e.g., image processor) that converts the X-ray data into X-ray images. In addition, the X-ray image apparatus 100 in accordance with an exemplary embodiment may further include the control unit 140 that controls an X-ray irradiation pattern of the X-ray generation unit 110.

The X-ray generation unit 110 generates X-rays and irradiates the object 35 with the generated X-rays. The X-ray generation unit 110 generates the X-rays by receiving power from a power supply unit (not shown). Here, energy of the X-rays can be controlled by a tube voltage, and a dose or an intensity of the X-rays can be controlled by a tube current or an exposure time of the X-rays.

The X-ray generation unit 110 may irradiate the object with monochromatic X-rays or polychromatic X-rays, but in the present exemplary embodiment, the X-ray generation unit 110 irradiates the object with the polychromatic X-rays, and an energy band of the irradiated X-rays is determined by an upper limit and a lower limit.

The X-ray generation unit 110 includes an X-ray tube 111 that generates X-rays.

Figure 4:
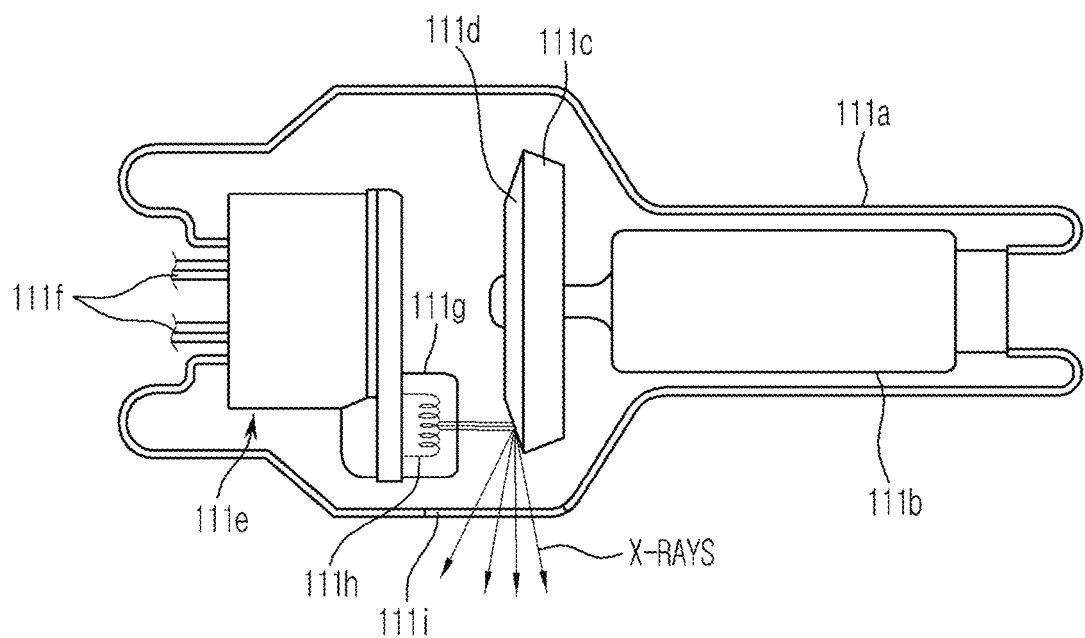
FIG. 4 illustrates a configuration of an X-ray tube.

FIG. 4 illustrates a configuration of an X-ray tube.

Referring to FIG. 4, the X-ray tube 111 may be implemented as a bipolar vacuum tube including an anode 111c and a cathode 111e, and the tube may be a glass tube 111a made of a rigid silicate glass or the like.

The cathode 111e includes a filament 111h and a focusing electrode 111g for focusing electrons, and the focusing electrode 111g may be referred to as a focusing cup. Thermoelectrons are generated in such a manner that the inside of the glass tube 111a is in a high vacuum state of about 10 mmHg and the filament 111h of the cathode is heated at a high temperature. A tungsten filament may be used as one example of the filament 111h, and the filament 111h may be heated by applying a current to an electric conductor 111f connected to the filament. However, the exemplary embodiments are not limited to an example of employing the filament 111h as the cathode 111e, and a carbon nanotube capable of being driven at a high-speed pulse may also be used as the cathode.

The anode 111c is generally made of copper, and a target material 111d is applied or disposed on a side of the anode 111c facing the cathode 111e. Here, as the target material, high-resistance materials such as Cr, Fe, Co, Ni, W, Mo, and the like may be used. As a melting point of the target material becomes higher, a focal spot size is reduced.

When a high voltage is applied between the cathode 111e and the anode 111c, thermoelectrons are accelerated and collide with the target material 111d, thereby generating X-rays. The generated X-rays are irradiated to the outside through a window 111i, and a beryllium (Be) thin film may be used as a material of the window.

The target material 111d may be rotated by a rotor 111b, and when the target material 111d is rotated, a heat accumulation factor may be increased 10 times or more per unit area in comparison with a case in which the target material 111d is fixed, and the focal spot size may be reduced.

The voltage applied between the cathode 111e and the anode 111c of the X-ray tube 111 may be referred to as a tube voltage, and a magnitude of the tube voltage may be displayed as a peak value kvp. When the tube voltage is increased, a speed of the thermoelectrons is increased and thereby the thermoelectrons collide with the target material to generate X-rays. As a result, energy of the generated X-rays (energy of photons) is increased. A current flowing in the X-ray tube 111 is referred to as a tube current, and may be displayed as an average value mA. When the tube current is increased, a dose of the X-rays (the number of photons of the X-rays) is increased.

Thus, an energy band of the X-rays can be controlled by the tube voltage, and an intensity or dose of the X-rays can be controlled by the tube current and an exposure time of the X-rays, and therefore an energy band and intensity of the irradiated X-rays can be controlled in accordance with types or characteristics of the object 35.

The X-ray generation unit 110 generates X-rays using the above-described X-ray tube 111, and irradiates the subject 30, more precisely, the object 35, with the generated X-rays.

When the X-ray generation unit 110 irradiates the object 35 with the X-rays, a degree of attenuation of the X-rays differs in accordance with a material inside the object 35 and the energy band of the irradiated X-rays. Here, a numerical representation of the degree of attenuation of the X-rays is called an attenuation coefficient.

First, the attenuation coefficient may be changed depending on the material inside the object 35.

Figure 5:
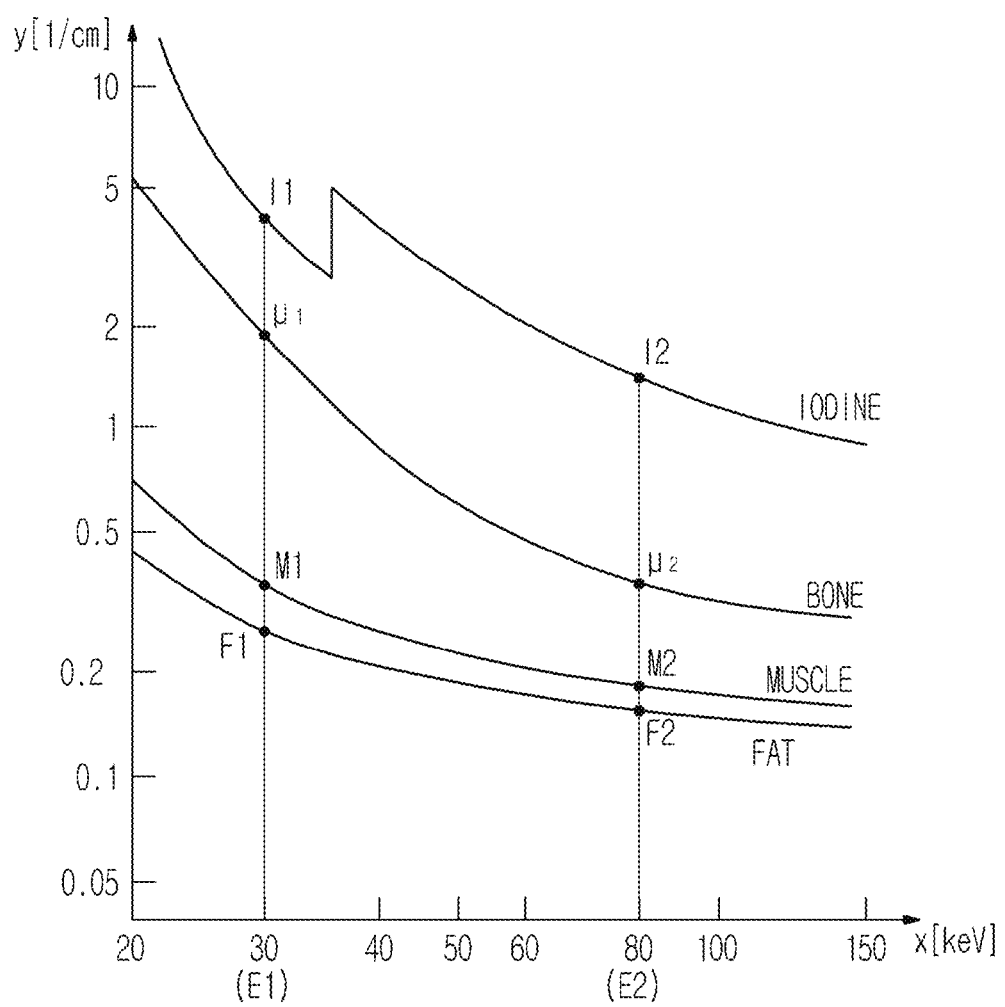
FIG. 5 is a graph illustrating a relationship between energy and an attenuation coefficient for each material inside an object.

This feature is illustrated in FIG. 5. FIG. 5 is a graph illustrating a relationship between energy and an attenuation coefficient for each material inside an object. An X-axis represents energy of photons irradiated to the object 35, and a Y-axis represents an attenuation coefficient.

Referring to the graph of FIG. 5, a curved line representing an attenuation coefficient of bones is located above a curved line representing an attenuation coefficient of soft tissue (muscle or fat), and a curved line representing an attenuation coefficient of iodine is located above the curved line representing the attenuation coefficient of bones. Specifically, when X-rays of the same energy band, for example, $E_1$, are irradiated, the attenuation coefficient $\mu_1$ of bones is larger than the attenuation coefficient $M_1$ of muscles, the attenuation coefficient $M_1$ of muscles is larger than the attenuation coefficient $F_1$ of fats, and the attenuation coefficient $I_1$ of iodine is larger than the attenuation coefficient $\mu_1$ of bones.

That is, mutually different materials inside the object 35 have mutually different attenuation coefficients, and the attenuation coefficient is increased as an atomic number or density of the material becomes higher.

Second, the attenuation coefficient may be changed depending on an energy band of the irradiated X-rays.

In the graph of FIG. 5, when the X-rays having energy bands $E_1$ and $E_2$ are respectively irradiated to bones which are materials inside the object 35, the attenuation coefficient in the lower energy band $\mu_1$ is larger than the attenuation coefficient in the higher energy band $\mu_2$. Even in a case in which the materials inside the object 35 are muscles or fats, it can be found that the attenuation coefficient $M_1$ or $F_1$ when the X-rays of the lower energy band $E_1$ are irradiated is larger than the attenuation coefficient $M_2$ or $F_2$ when the X-rays of the higher energy band $E_2$ are irradiated. In addition, the same result can be found in the iodine.

That is, as the energy band of the X-rays irradiated to the object 35 becomes lower, the attenuation coefficient may be increased.

Such an attenuation coefficient may be represented as the following Equation 1:

$$I=I_0 \cdot e^{-\mu(E) \cdot T} I=I_0 \cdot e^{-\mu(E) \cdot T} \qquad \text{[Equation 1]}$$

Here, $I_0$ denotes an intensity of X-rays irradiated on a material, I denotes an intensity of X-rays transmitted through the material, and $\mu(E)$ denotes an attenuation coefficient of the material with respect to X-rays having energy E. T denotes a thickness of the material through which the X-rays are transmitted.

In Equation 1, it can be seen that an intensity of the transmitted X-rays is reduced as the attenuation coefficient is increased (that is, as hardness of the material increases or as the energy band of the X-rays decreases) and a thickness of the material is increased.

In order to obtain X-ray images of dynamic organs, such as blood vessels, imaging is required to be performed a plurality of times. Thus, in general, a user sets an imaging cycle through the input unit 171, and X-rays are irradiated to the object 35 for each cycle, so that a change in the object over time may be reflected in the X-ray images.

In this instance, in order to obtain blood vessel X-ray images, an energy band of the irradiated X-rays can be changed. That is, since an attenuation coefficient of iodine that is a component of a contrast medium differs in accordance with the energy band of the irradiated X-rays, only images of blood vessels can be separated from the X-ray images.

To achieve this result, the X-rays of a plurality of energy bands having a fixed cycle may be generated, and sequentially irradiated to the object 35. In order to reduce errors (motion artifacts) due to irradiation time differences among the sequentially irradiated X-rays in this process, the X-rays may be non-uniformly irradiated. This will be described later.

Referring again to FIG. 3, the X-ray detection unit 120 detects the X-rays transmitted through the object 35, and converts the detected X-rays into electric signals to acquire X-ray data.

In general, the X-ray detection unit 120 may be classified according to the method of constituting materials, the method of converting the detected X-rays into the electric signals, and the method of acquiring the X-ray data, and various methods through which the X-ray detection unit detects the X-rays and converts the detected X-rays into the electric signals to acquire the X-ray data will be described herein.

First, the X-ray detection unit 120 is classified according to the method by which the X-ray detection unit 120 converts the X-rays into the electric signals, which may be a direct conversion method or an indirect conversion method.

In the direct conversion method, when the X-rays are irradiated, pairs of electrons and holes are temporarily created inside a light receiving element, and the electrons and the holes are respectively moved to the anode and the cathode by an electric field applied to both ends of the light receiving element. Here, the X-ray detection unit converts such movement into electric signals. In the direct conversion method, as a material of the light receiving element, a-Se, CdZnTe, $HgI_2$, $PbI_2$, or the like may be used.

In the indirect conversion method, a scintillator is provided between the light receiving element and the X-ray generation unit, photon having a wavelength in a visible light region are emitted by a reaction between the X-rays irradiated from the X-ray generation unit and the scintillator, and then the light receiving element detects the emitted photons and converts the detected photons into electric signals. As a material of the light receiving element in the indirect conversion method, a-Si or the like may be used, and as the scintillator, a GADOX scintillator in the form of a thin film, a micro-columnar or needle-like CSI (T1), or the like may be used.

In addition, the X-ray detection unit is classified according to a method by which the X-ray detection unit acquires the X-ray data, which may be a charge integration mode for storing charge for a certain period of time and then acquiring signals from the stored charge or a photon counting mode for counting photons having an energy of a threshold energy or more whenever signals are generated by a single X-ray photon.

Meanwhile, there is no limitation on a material constituting method of the X-ray detection unit 120 or a conversion method of electric signals, but in the following exemplary embodiments which will be described herein, a direct conversion method of directly acquiring electric signals from X-rays and a hybrid method of combining a light receiving element for detecting X-rays and a read circuit chip will be applied for convenience of description.

The X-ray detection unit 120 detects the X-rays transmitted through the object 35, and converts the detected X-rays into electric signals to output the converted signals.

The image processing unit 130 may acquire an X-ray image based on the X-ray data transmitted from the X-ray detection unit 120. In particular, when acquiring a blood vessel X-ray image, the image processing unit 130 may separate a desired internal tissue from the X-ray data to acquire the blood vessel X-ray image.

The image processing unit 130 may include an image generation unit 131 that generates an X-ray image from the transmitted X-ray data, and a material separation unit 132 that separates a desired internal material from the acquired X-ray image. In addition, the image processing unit 130 may further include a reference data providing unit 133 that provides reference data through the image transmitted from the material separation unit 132 again to the material separation unit 132.

Hereinafter, with reference to FIGS. 5 to 7, each component of the image processing unit 130 using an energy subtraction method will be described in comparison with a conventional temporal subtraction method.

Figure 6:
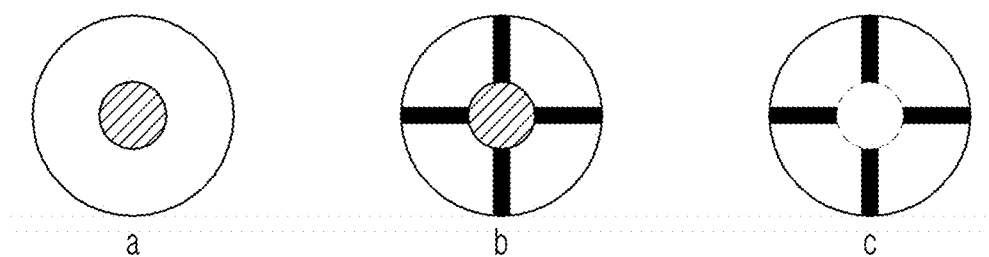
FIG. 6 is a schematic diagram illustrating an X-ray image used in a conventional temporal subtraction method.

FIG. 6 is a schematic diagram illustrating an X-ray image used in a conventional subtraction method. "a" of FIG. 6 indicates a mask image. The mask image indicates an X-ray image acquired from the object 35 before a contrast medium is injected. "b" of FIG. 6 indicates an X-ray image acquired from the object 35 into which the contrast medium is injected. "c" of FIG. 6 indicates a blood vessel X-ray image finally acquired by the temporal subtraction method.

In general, blood vessels are not visible in a simple X-ray image. However, when the contrast medium is injected into the blood vessels and radiography is performed, the shapes of the blood vessels can be confirmed through the radiography. This method is called angiography.

Figure 7A:
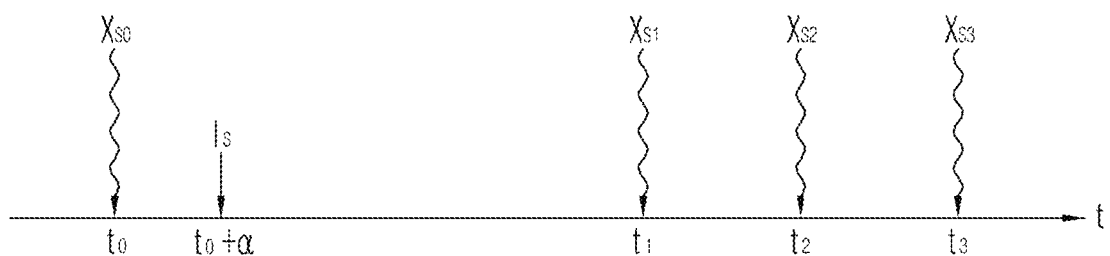
FIG. 7A is a diagram illustrating a method of generating X-rays in accordance with a conventional temporal subtraction method.
Figure 7B:
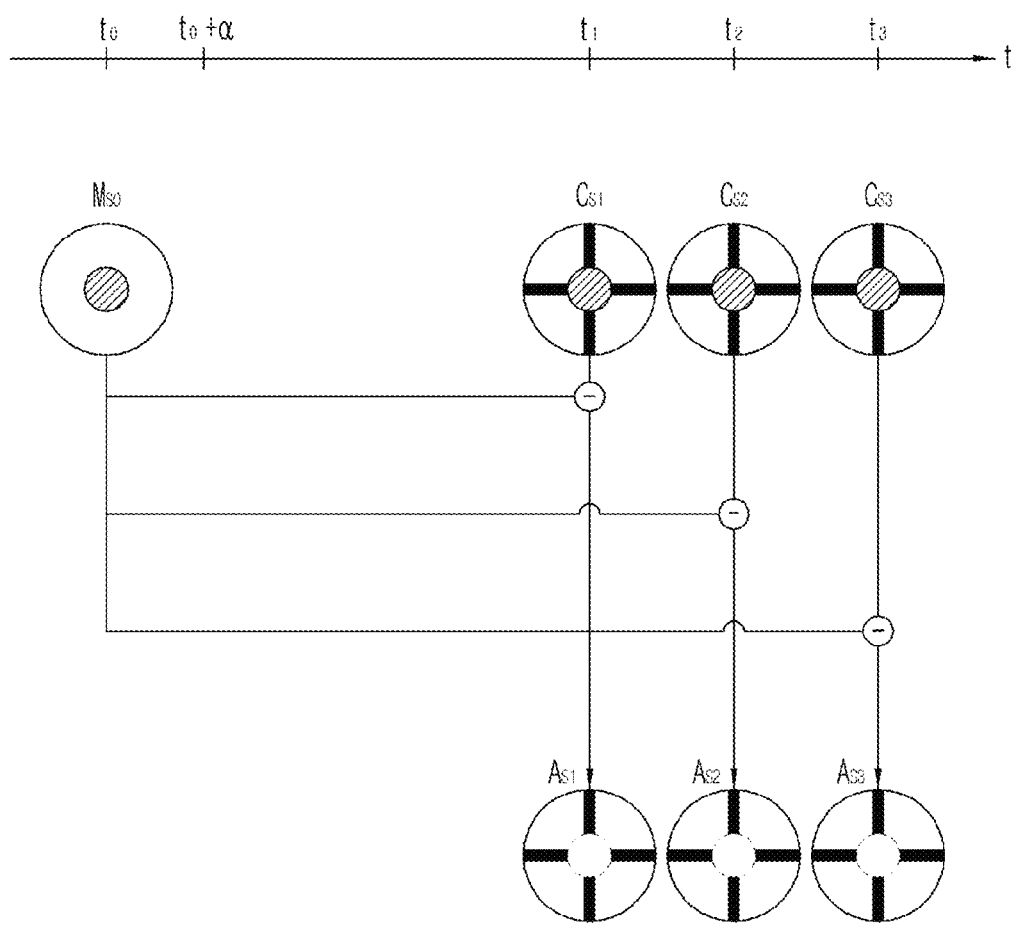
FIG. 7B is a diagram illustrating a method of acquiring a blood vessel X-ray image in accordance with a conventional temporal subtraction method.

The temporal subtraction method is one type of angiography technology. FIGS. 7A and 7B are diagrams illustrating a method of acquiring a blood vessel X-ray image in accordance with the conventional temporal subtraction method. X-rays irradiated in accordance with the temporal subtraction method have a single polychromatic spectrum.

FIG. 7A is a diagram illustrating a method of generating X-rays in accordance with a conventional temporal subtraction method. $X_{S0}$, $X_{S1}$, $X_{S2}$, and $X_{S3}$ indicate single energy X-rays whose irradiation time points are respectively $t_0$, $t_1$, $t_2$, and $t_3$. $I_S$ indicates a contrast medium injected into the object 35 at a time point of $t_0+\alpha$. FIG. 7B is a diagram illustrating a method of acquiring a blood vessel X-ray image in accordance with a conventional temporal subtraction method. $M_{S0}$ indicates a mask image acquired at a time point of $t_0$, and $C_{S1}$, $C_{S2}$, and $C_{S3}$ indicate single energy X-ray images acquired at time points $t_1$, $t_2$, and $t_3$ after the contrast medium is injected. $A_{S1}$, $A_{S2}$, and $A_{S3}$ indicate blood vessel X-ray images extracted at time points $t_1$, $t_2$, and $t_3$ after the contrast medium is injected.

As shown in FIG. 7A, in order to acquire a mask image that is an image before injecting the contrast medium into the object 35, single energy X-rays $X_{S0}$ are irradiated at a time point $t_0$. $M_{S0}$ that is a mask image of (b) of FIG. 6 can be acquired from the irradiated X-rays $X_{S0}$. A contrast medium $I_S$ is injected into the object 35 at a time point $t_0+\alpha$ when a predetermined time elapses from the time point $t_0$. In order to acquire the blood vessel image, single energy X-rays $X_{S1}$ are irradiated at a desired time point $t_1$ after a sufficient time elapses so that the contrast medium spreads through the blood vessels.

The image generation unit may acquire an X-ray image $C_{S1}$ after injection of the contrast medium at the time point $t_1$ from the X-rays $X_{S1}$ irradiated in this manner. Consequently, when comparing the X-ray image $C_{S1}$ after injection of the contrast medium and the mask image $M_{S0}$, a blood vessel X-ray image $A_{S1}$ at the time point $t_1$ may be extracted.

According to the temporal subtraction method, there may be a time difference between acquisition time points of the two images. As described above, such a time difference may occur because the X-ray image is acquired after the sufficient time elapses so that the contrast medium spreads within the blood vessels to a prescribed extent. For example, as shown in FIGS. 7A and 7B, there may be a time difference between an acquisition time point $t_0$ of the mask image and a subsequent irradiation time point $t_1$ of X-rays.

Such a time difference may cause occurrence of an error in the extracted blood vessel X-ray image. Based on the comparison between the X-ray image after the contrast medium is injected and the mask image, when a structural difference of the background and contrast coincide with each other, only the blood vessel area can be accurately extracted. However, when a patient, that is, the subject 30, moves while the contrast medium is spreading, for example, when there is movement caused by breathing of the patient or movement of internal organs caused by cardiac impulse of the patient, geometric deformation of the X-ray image may occur. Alternatively, a unique movement such as contraction or expansion of the object 35 may cause occurrence of an error in extraction of the blood vessel area.

Figure 8A:
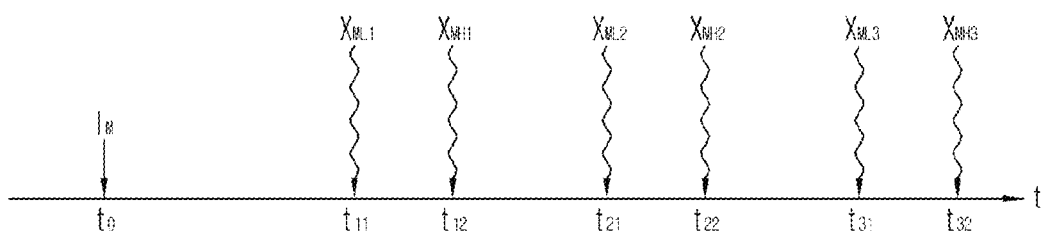
FIG. 8A is a diagram illustrating a method of generating X-rays in accordance with an energy subtraction method.
Figure 8B:
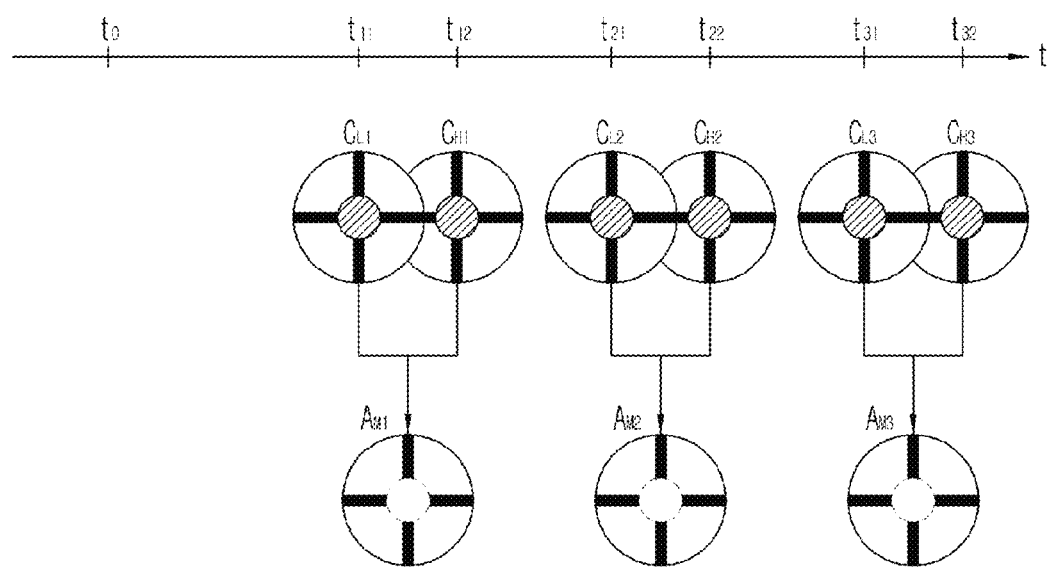
FIG. 8B is a diagram illustrating a method of acquiring a blood vessel X-ray image in accordance with an energy subtraction method.

In order to reduce such an error, an energy subtraction method may be used. The energy subtraction method is also one angiography technology like the temporal subtraction method. FIG. 8 is a diagram illustrating an energy subtraction method. Unlike the temporal subtraction method using the single energy X-rays, X-rays of mutually different energy bands are irradiated on the object 35. In FIGS. 8A and 8B, cases in which low energy X-rays and high energy X-rays are irradiated on the object 35 will be described. Here, a high energy band and a low energy band are relative concepts, and may vary depending on the object 35.

FIG. 8A is a diagram illustrating a method of generating X-rays in accordance with an energy subtraction method. $X_{ML1}$, $X_{ML2}$, and $X_{ML3}$ indicate low energy X-rays whose irradiation time points are $t_{11}$, $t_{21}$, and $t_{31}$, and $X_{MH1}$, $X_{MH2}$, and $X_{MH3}$ indicate high energy X-rays whose irradiation time points are $t_{12}$, $t_{22}$, and $t_{32}$. $I_M$ indicates a contrast medium injected into the object 35 at the time point of $t_0$. FIG. 8B is a diagram illustrating a method of acquiring a blood vessel X-ray image in accordance with the energy subtraction method. $C_{L1}$, $C_{L2}$, and $C_{L3}$ indicate low energy X-ray images acquired at time points $t_{11}$, $t_{21}$, and $t_{31}$ after injection of the contrast medium, and $C_{H1}$, $C_{H2}$, and $C_{H3}$ indicate high energy X-ray images acquired at the time points $t_{12}$, $t_{22}$, and $t_{32}$ after injecting the contrast medium. In addition, $A_{M1}$, $A_{M2}$, and $A_{M3}$ indicate blood vessel X-ray images acquired at the time points $t_1$, $t_2$, and $t_3$ after injection of the contrast medium.

As shown in FIG. 8A, the contrast medium $I_M$ is injected into the object 35 before irradiating the X-rays. In order to obtain the blood vessel image, sufficient time is required after injection of the contrast medium so that the contrast medium spreads through the blood vessels.

First, in order to acquire X-ray images corresponding to two different energy bands, the X-ray generation unit 110 irradiates the object with X-rays. To irradiate the X-rays, the X-ray generation unit 110 irradiates the object with X-rays of a high energy band and X-rays of a low energy band. Alternatively, the X-ray generation unit 110 may irradiate the object with broadband X-rays including the two energy bands together, and the X-ray detection unit 120 may detect and separate the X-rays into the high energy band and the low energy band. The X-ray detection unit 120 in the X-ray image apparatus and the control method for the X-ray image apparatus in accordance with an exemplary embodiment will be described herein under the assumption that X-rays of the high energy band and the low energy band are sequentially irradiated. Referring to FIG. 8A, at the time points of $t_{11}$ and $t_{12}$ when the sufficient time for the contrast medium to spread has elapsed, low energy X-rays $X_{ML1}$ and high energy X-rays $X_{MH1}$ are irradiated.

When desiring to separate two kinds of materials from the X-ray image, materials desired to be separated should have different X-ray attenuation characteristics from each other, and X-ray images corresponding to mutually different energy bands should be acquired. To achieve this result, the image generation unit 131 may generate X-ray images corresponding to mutually different energy bands. For example, as shown in FIG. 8B, the image generation unit 131 may sequentially generate a low energy X-ray image $C_{L1}$ and a high energy X-ray image $C_{H1}$ after injecting the contrast medium so as to correspond to the X-rays $X_{ML1}$ and $X_{MH1}$.

A brightness difference between the contrast medium (blood vessels; lumens) and body constituents (for example, bones, calcified tissues, and the like) not including the contrast medium which are internal materials to be separated from the X-ray images $C_{L1}$ and $C_{H1}$ generated in this manner appears differently. This is because a difference in attenuation characteristics of the internal materials is different for each energy band.

The material separation unit 132 separates a blood vessel image from an original image generated in the image generation unit 131. The material separation unit 132 may separate two material images by performing two operations such as multiplying at least one of the two X-ray images $C_{L1}$ and $C_{H1}$ by a weighted value and then performing subtraction. This is called dual-energy X-ray absorptiometry.

For example, in order to separate blood vessels from bones and calcified tissues, a blood vessel image can be acquired by multiplying a low-energy X-ray image $C_{L1}$ by a certain weighted value and then subtracting the multiplication result from a high-energy X-ray image $C_{H1}$. That is, images in which bones and calcified materials are removed and blood vessels are clearly visible can be acquired.

As another example, when the number of materials desired to be separated is three or more including blood vessels, the image generation unit 131 may generate at least three X-ray images respectively corresponding to at least three energy bands, and the material separation unit 132 may separate at least three material images including blood vessels by multiplying each image by a proper weighted value and then performing subtraction.

As described above, the X-ray image apparatus 100 does not have limitations in the number of materials to be separated, and may acquire an original image in accordance with the number of materials desired to be separated and separate each material image using attenuation characteristics for each material.

In addition, the method of separating the material image by multiplying the image by the weighted value and performing subtraction is merely one method which can be used in the material separation unit 132, and a material separation algorithm for predicting a thickness of each material such as polynomial regression can be used instead of the method of separating the material image.

In this manner, the material separation unit 132 may generate a blood vessel X-ray image $A_{M1}$ using the X-ray images $C_{L1}$ and $C_{L2}$. Consequently, by sequentially irradiating the object with low-energy X-rays and high-energy X-rays, a single corresponding blood vessel X-ray image can be acquired.

In the energy subtraction method, a difference (several to several hundred ms) in acquisition time points of the low-energy image and the high-energy image, which are the basis for multi-energy based blood vessel X-ray images, is smaller than a time difference between a mask image acquisition time point and the X-ray image acquisition time point after injection of the contrast medium in the temporal subtraction method. This is because the time difference between the mask image acquisition time point and the X-ray image acquisition time point after injection of the contrast medium becomes larger over time because a new mask image cannot be acquired while the contrast medium spreads in the temporal subtraction method, but in the energy subtraction method, the mask image is not required and a difference in the acquisition time points between the X-ray images corresponding to mutually different energy bands is constant.

Thus, when the energy subtraction method is applied, a time during which movement of the object 35 or the subject 30 occurs is shorter. As a result, the number of errors that can occur by the movement of the object 35 or the subject 30 during the difference between the acquisition time points of the two images in the multi-energy based angiography method may be smaller than that in the temporal subtraction method.

Referring again to FIG. 3, the control unit 140 may control operations of the X-ray generation unit 110 so that a process of sequentially irradiating the object with the multi-energy X-rays is repeated for each fixed cycle. Through this process, the blood vessel X-ray images may be repeatedly acquired for each fixed cycle.

When the temporal subtraction method that is the conventional angiography method is repeatedly performed as shown in FIGS. 7A and 7B, a plurality of blood vessel X-ray images may be acquired. Specifically, X-ray images $C_{S2}$ and $C_{S3}$ after injection of the contrast medium are acquired by irradiating the object with X-rays $X_{S2}$ and $X_{S3}$ at the time points $t_2$ and $t_3$, and blood vessel X-ray images $A_{S2}$ and $A_{S3}$ at the time points $t_2$ and $t_3$ may be extracted by comparing the X-ray images $C_{S2}$ and $C_{S3}$ and the mask image $M_{S0}$. In this manner, a plurality of blood vessel X-ray images $A_{S1}$, $A_{S2}$, and $A_{S3}$ may be acquired and provided to users in the form of moving images.

In this case, as irradiation of X-rays is repeatedly performed, a difference (difference between $t_0$ and $t_1$, difference between $t_0$ and $t_2$, or difference between $t_0$ and $t_3$) between an acquisition time point of the X-ray image and an acquisition time point of the mask image becomes larger, and therefore the above-described error is more likely to occur.

The X-ray image with respect to blood vessels may be acquired by repeatedly performing the energy subtraction method for each fixed cycle, thereby providing a moving image indicating a blood flow to a user. In this instance, by using the energy subtraction method, the error caused by the movement may be further reduced.

As shown in FIGS. 8A and 8B, low energy X-ray images $C_{L2}$ and $C_{L3}$ after injection of the contrast medium are acquired by irradiating the object with X-rays $X_{ML2}$ and $X_{MH2}$ at time points $t_{21}$ and $t_{22}$ and irradiating the object with X-rays $X_{ML3}$ and $X_{MH3}$ at the time points $t_{31}$ and $t_{32}$, and high energy X-ray images $C_{H2}$ and $C_{H3}$ are acquired. Consequently, a blood vessel X-ray image $A_{M2}$ may be acquired using the X-ray images $C_{L2}$ and $C_{H2}$, and a blood vessel X-ray image $A_{M3}$ may be acquired using the X-ray images $C_{L3}$ and $C_{H3}$. When sequentially observing the blood vessel X-ray images $A_{M1}$, $A_{M2}$, and $A_{M3}$ based on the acquisition time point, movement of the blood flow over time can be confirmed.

Unlike the temporal subtraction method in which the X-ray image and the mask image should be compared whenever the X-ray image is acquired in accordance with a change in the time point, the energy subtraction method may compare only the X-ray images ($C_{L1}$ and $C_{H1}$, $C_{L2}$ and $C_{H2}$, and $C_{L3}$ and $C_{H3}$) corresponding to mutually different energy bands of the X-rays ($X_{ML1}$ and $X_{MH1}$, $X_{ML2}$ and $X_{MH2}$, and $X_{ML3}$ and $X_{MH3}$) belonging to the same cycle. Such an X-ray image may be repeatedly acquired for each cycle, and a difference between acquisition time points (difference between $t_{11}$ and $t_{12}$, difference between $t_{21}$ and $t_{22}$, and difference between $t_{31}$ and $t_{32}$) of the X-ray images belonging to the same cycle is not large, and therefore a probability of occurrence of the error caused by the movement may be reduced.

The control unit 140 may control operations of the X-ray generation unit 110 so that multi-energy X-rays are non-uniformly irradiated during a single cycle. Here, the term non-uniformity may indicate that an irradiation interval of the irradiated plurality of X-rays is not the same.

Figure 9A:
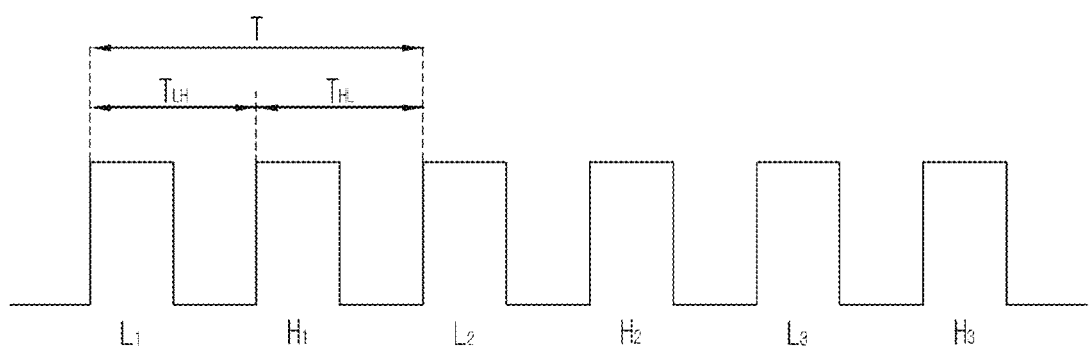
FIG. 9A is a diagram illustrating an X-ray pulse generated when multi-energy X-rays are sequentially irradiated in a uniform manner.
Figure 9B:
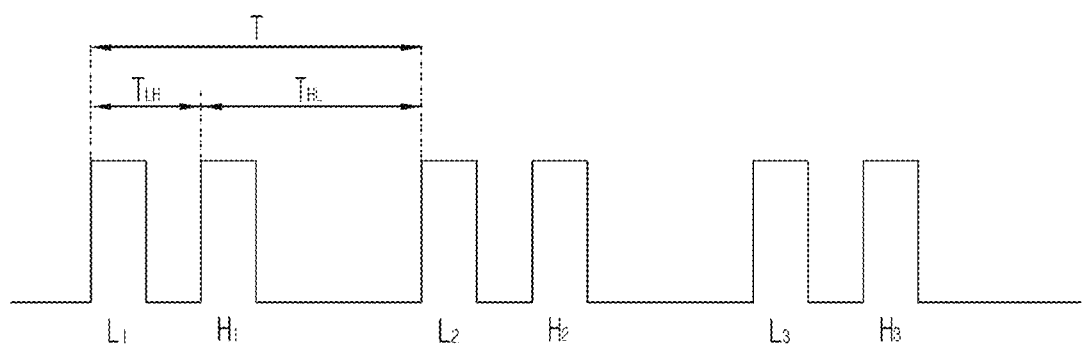
FIG. 9B is a diagram illustrating an X-ray pulse generated when multi-energy X-rays are sequentially irradiated in a non-uniform manner.

FIGS. 9A and 9B are diagrams illustrating an X-ray pulse irradiated in accordance with an energy subtraction method. Here, it is assumed that multi-energy X-rays have high energy and low energy. FIG. 9A is a diagram illustrating an X-ray pulse generated when multi-energy X-rays are sequentially irradiated in a uniform manner, and FIG. 9B is a diagram illustrating an X-ray pulse generated when multi-energy X-rays are sequentially irradiated in a non-uniform manner.

When desiring to irradiate the object 35 with the multi-energy X-rays for each fixed cycle, a user may input a cycle of the irradiated X-ray pulse. In this case, the multi-energy X-rays may be uniformly irradiated during the input cycle.

For example, as shown in FIG. 9A, when low energy X-rays and high energy X-rays are uniformly and sequentially irradiated in a cycle T, an irradiation interval between low energy X-rays $L_1$ and high energy X-rays $H_1$ which are involved in a single blood vessel X-ray image is $T_{LH}$, and an irradiation interval between low energy X-rays $L_2$ and high energy X-rays $H_1$ which are involved in mutually different blood vessel X-ray images is $T_{HL}$. In this instance, the multi-energy X-rays are uniformly irradiated, and therefore $T_{LH}$ and $T_{HL}$ have the same value.

As described above, there is a time difference $T_{LH}$ between the acquisition time points of the low energy X-ray image and the high energy X-ray image which are the basis when the blood vessel X-ray images are acquired. Although this is a shorter time than that in the temporal subtraction method, there is a probability of occurrence of the movement of the subject 30 or the object 35. Thus, the probability of occurrence of the movement of the subject 30 or the object 35 should be reduced by reducing the time difference $T_{LH}$.

In FIG. 9B, low energy X-rays and high energy X-rays are non-uniformly irradiated in a cycle T. Specifically, an irradiation interval between low energy X-rays $L_1$ and high energy X-rays $H_1$ which are involved in a single blood vessel X-ray image is $T_{LH}$, and an irradiation interval between low energy X-rays $L_2$ and high energy X-rays $H_1$ which are involved in mutually different blood vessel X-ray images is $T_{HL}$. As can be seen in FIG. 9B, since the multi-energy X-rays are non-uniformly irradiated, $T_{LH}$ and $T_{HL}$ are different from each other.

In particular, in order to reduce an error due to movement of the subject 30 or the object 35 which may occur when acquiring the blood vessel X-ray images, $T_{LH}$ should be smaller than $T_{HL}$. An irradiation interval $T_{HL}$ of X-rays which are involved in mutually different blood vessel X-ray images does not affect the respectively acquired blood vessel X-ray images even if the irradiation interval $T_{HL}$ is significantly long. However, as the irradiation interval of the X-rays which are involved in generation of the single blood vessel X-ray image is shorter, a probability of occurrence of the movement of the subject 30 or the object 35 may be reduced. Thus, as $T_{LH}$ becomes smaller, a more accurate blood vessel X-ray image may be acquired.

Figure 10:
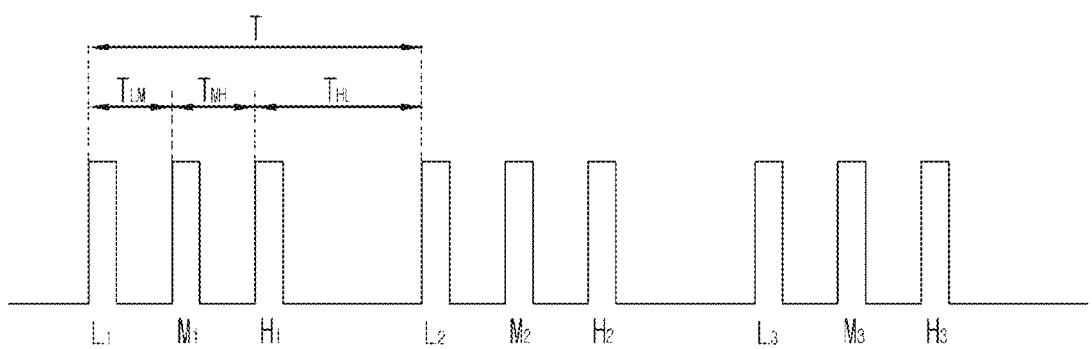
FIG. 10 is a diagram illustrating an X-ray pulse generated when X-rays with three kinds of energy are irradiated in a non-uniform manner.

In FIGS. 9A and 9B, angiography based on X-rays having two kinds of energy, that is, low energy X-rays and high energy X-rays, has been described, but an energy type of the irradiated X-rays is not limited thereto. As shown in FIG. 10, the X-rays having three kinds of energy may be non-uniformly irradiated. $L_1$, $L_2$, and $L_3$ refer to low energy X-rays, $M_1$, $M_2$, and $M_3$ refer to medium energy X-rays, and $H_1$, H2, and H3 refer to high energy X-rays.

Like the angiography based on the X-rays having two kinds of energy, as an irradiation interval of the X-rays which are involved in acquisition of a single blood vessel X-ray image is shorter, a probability of occurrence of error may be reduced. Thus, when the low energy, the medium energy, and the high energy X-rays are sequentially irradiated, the irradiation interval therebetween should be non-uniform.

In FIG. 10, low energy X-rays, medium energy X-rays, and high energy X-rays may be non-uniformly irradiated in a cycle T. Specifically, an irradiation interval between low energy X-rays $L_1$ and medium energy X-rays $M_1$ which are involved in a single blood vessel X-ray image is $T_{LM}$, and an irradiation interval between the medium energy X-rays $M_1$ and high energy X-rays $H_1$ which are involved in the same single blood vessel X-ray images is $T_{MH}$. In addition, an irradiation interval between the high energy X-rays $H_1$ and the low energy X-rays $L_2$ which are involved in mutually different blood vessel X-ray images is $T_{HL}$.

As can be seen in FIG. 10, since the multi-energy X-rays are non-uniformly irradiated, $T_{LM}$ and $T_{MH}$ are small, and $T_{HL}$ is larger than $T_{LM}$ and $T_{MH}$. $T_{LM}$ and $T_{MH}$ indicate an irradiation time difference of X-rays which are involved in the same blood vessel X-ray image, and therefore the irradiation interval is reduced by non-uniformly irradiating the object 35 with the X-rays, thereby reducing a probability of occurrence of error.

The material separation unit 132 may generate a blood flow information image by combining the plurality of blood vessel X-ray images into one image. This will be described later.

Referring again to FIG. 3, the reference data providing unit 133 may provide reference data when correcting the blood vessel X-ray image separated from the material separation unit 132.

The reference data providing unit 133 may provide the mask image that is the X-ray image before injection of the contrast medium to the material separation unit 132. The mask image may be acquired prior to performing the energy subtraction method or acquired by separating the contrast medium from the X-ray image by the material separation unit, but these acquiring techniques are merely examples. Thus, it is sufficient that the mask image be provided when the material separation unit 132 separates the blood vessel X-ray image.

The reference data providing unit 133 may provide the mask image before injection of the contrast medium, so that the mask image before injection of the contrast medium and the X-ray image after injection of the contrast medium can be compared. Through this process, the blood vessel X-ray image in which an internal change or the like of the object 35 caused by the contrast medium is removed.

In addition, the reference data providing unit 133 may provide a difference between X-ray data corresponding to the same energy band as reference data. Since there is always an error due to the movement of the subject 30 or the object 35 when the blood vessel X-ray image is acquired, the error is required to be corrected. Thus, a difference between the X-ray data whose acquisition time points are adjacent to each other among the X-ray data corresponding to the same energy band may be obtained, and the blood vessel X-ray image may be corrected using the obtained difference.

In addition, such a difference may reflect the result according to the blood flow, and therefore whether such a difference is a difference due to the movement or a difference according to the blood flow may be determined and correction for the difference may be performed.

Referring again to FIG. 3, the display unit 172 may display the blood vessel X-ray image acquired in the image processing unit 130 on a screen. A cathode ray tube (CRT), a liquid crystal display (LCD), an organic light emitting diode (OLED), or the like may be applied as the display unit 172, but the display unit 172 is not limited thereto.

The display unit 172 may separate the acquired plurality of blood vessel X-ray images in accordance with the acquisition time points, and display the separated blood vessel X-ray images on a single screen. The display unit 172 may receive the blood vessel X-ray images repeatedly generated for each fixed cycle by the image processing unit 130. The display unit 172 may display the received plurality of blood vessel X-ray images on the single screen, so that a user may confirm the blood flow.

Figure 11:
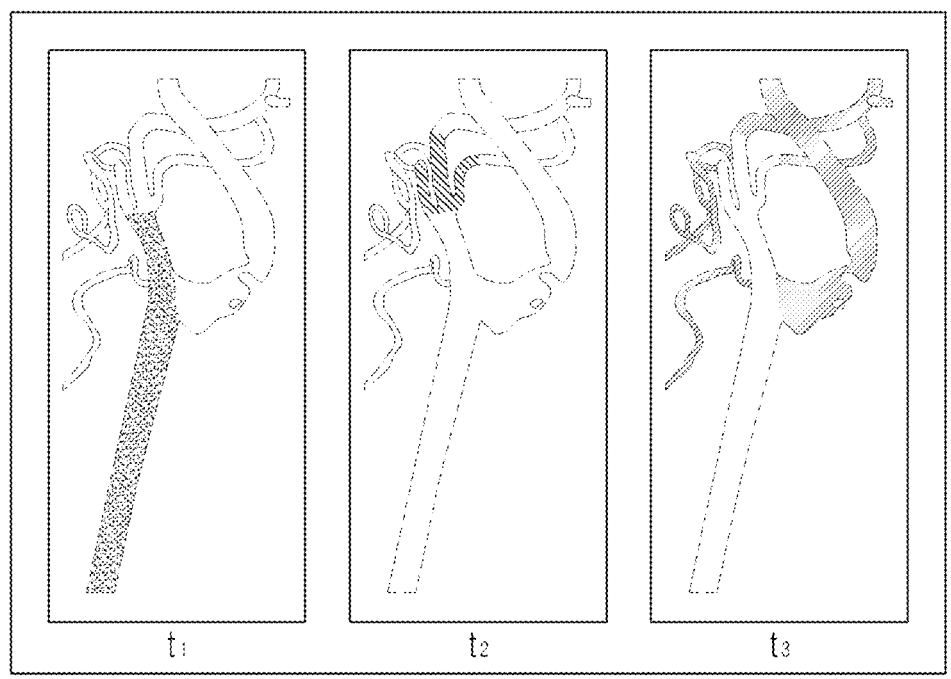
FIG. 11 is a diagram illustrating a screen in which blood vessel X-ray images are classified in accordance with an acquisition time point and simultaneously displayed.

FIG. 11 is a diagram illustrating a screen in which a blood vessel X-ray image is classified in accordance with an acquisition time point and simultaneously displayed. The blood vessel X-ray images may be displayed on a single screen in an order in which the blood vessel X-ray images are acquired, and acquisition time points may be displayed together with the blood vessel X-ray images. A portion represented by a dotted line indicates a contour of all of the blood vessels for clarity of understanding, and may not be displayed on the screen. A dark portion is an area in which a contrast medium is present, and shapes of the blood vessels and blood flow information such as a direction of blood flow may be predicted through the dark portion.

It can be seen that a blood flow is located in a low portion of the blood vessel X-ray image acquired at a first time point $t_1$. It can be seen that, in the blood vessel X-ray image acquired at the following time point $t_2$, the blood flow is located above the location of the blood flow confirmed through the blood vessel X-ray image acquired at the time point $t_1$. Thus, it can be found that the blood flow flows upward from a bottom of the screen along the blood vessels. In the blood vessel X-ray image acquired at a final time point $t_3$, it can be seen that the blood flow confirmed through the blood vessel X-ray image acquired at the time point $t_2$ moves in a different direction through the blood vessels.

Figure 12:
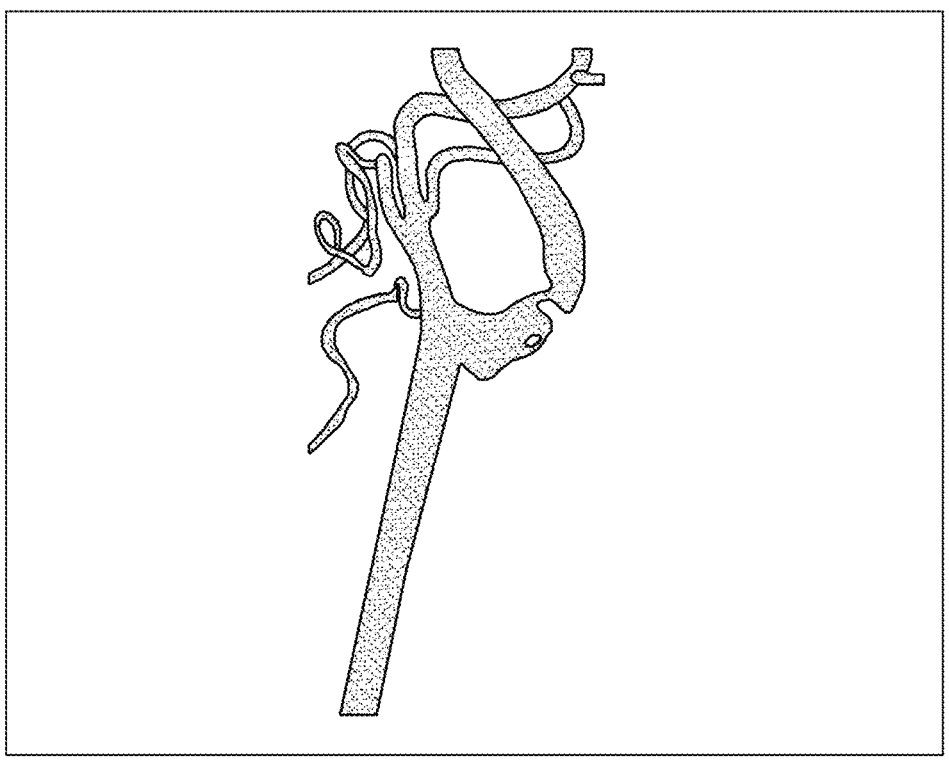
FIG. 12 is a diagram illustrating a screen in which a plurality of blood vessel X-ray images are overlapped and displayed.

The display unit 172 may overlap the plurality of blood vessel X-ray images acquired by the image processing unit 130 and display the overlapped image on the screen. FIG. 12 is a diagram illustrating a screen in which the plurality of blood vessel X-ray images of FIG. 11 are overlapped and displayed. An advancing direction of the blood flow in accordance with the time point and a shape of the blood vessel observed at each time point can be confirmed through FIG. 11, and the plurality of blood vessel X-ray images are overlapped and displayed on a single screen as shown in FIG. 12, thereby enabling a shape of all of the blood vessels to be confirmed. When the shape of all of the blood vessels is confirmed, a user may easily determine whether there is an abnormality in the blood vessels.

Figure 13:
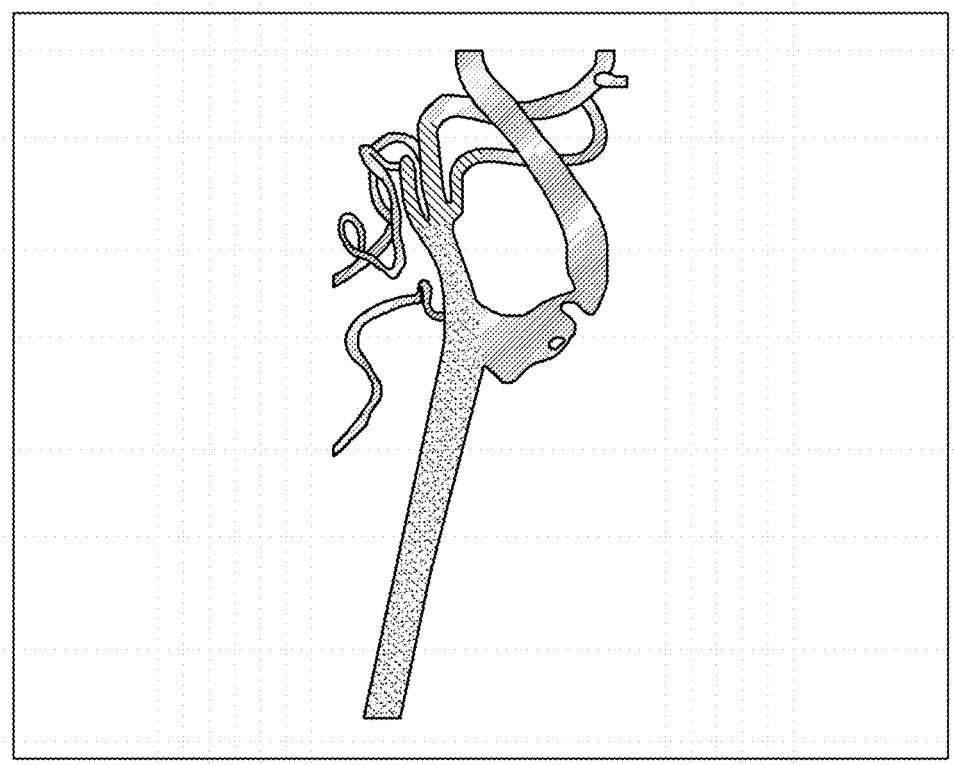
FIG. 13 is a diagram illustrating a screen in which a color or a shade of a blood vessel area in a blood vessel X-ray image is differentiated in accordance with an acquisition time point of the image to be displayed.

The plurality of blood vessel X-ray images are overlapped and displayed, and a color or a shade of the plurality of blood vessel X-ray images may be differentiated and displayed as shown in FIG. 13. When the plurality of blood vessel X-ray images are displayed on the screen in this manner, the shape of all of the blood vessels can be confirmed, and the orientation of the blood flow can also be confirmed. When the plurality of blood vessel X-ray images is displayed on the screen in this manner, the displayed images can assist in diagnosis of vascular diseases such as arteriosclerosis or cerebral hemorrhaging.

Alternatively or in addition, the display unit 172 may display, on the screen, blood flow information internally confirmed by the X-ray image apparatus. Based on the overlapped image of FIG. 13, a contour, a length, and a diameter of the blood vessel and blood flow information such as an advancing direction or an advancing speed of the blood flow may be displayed on the screen. Such blood flow information can be confirmed by an internal computation of the X-ray image apparatus. Through this feature, a user can more accurately confirm the blood flow information of the subject 30, and take corresponding action.

Alternatively, unlike the simple overlapped image, a blood vessel X-ray moving image which expresses a blood flow in the actual blood vessel may be displayed on the screen.

First, the material separation unit 132 may convert the plurality of blood vessel X-ray images whose acquisition time points are different from each other into a single blood vessel X-ray moving image. That is, the blood flow information image may include information about the blood flows flowing through the blood vessels between the time point at which the first blood vessel X-ray image is acquired and the time point at which the final blood vessel X-ray image is acquired.

When the blood flow information image is generated, the display unit 172 may display the blood vessel X-ray moving image on the screen. Through this blood flow information image, the blood flow information in accordance with a change in the time point can be visually acquired rather than confirming the blood flow at the specific time point.

Figure 14:
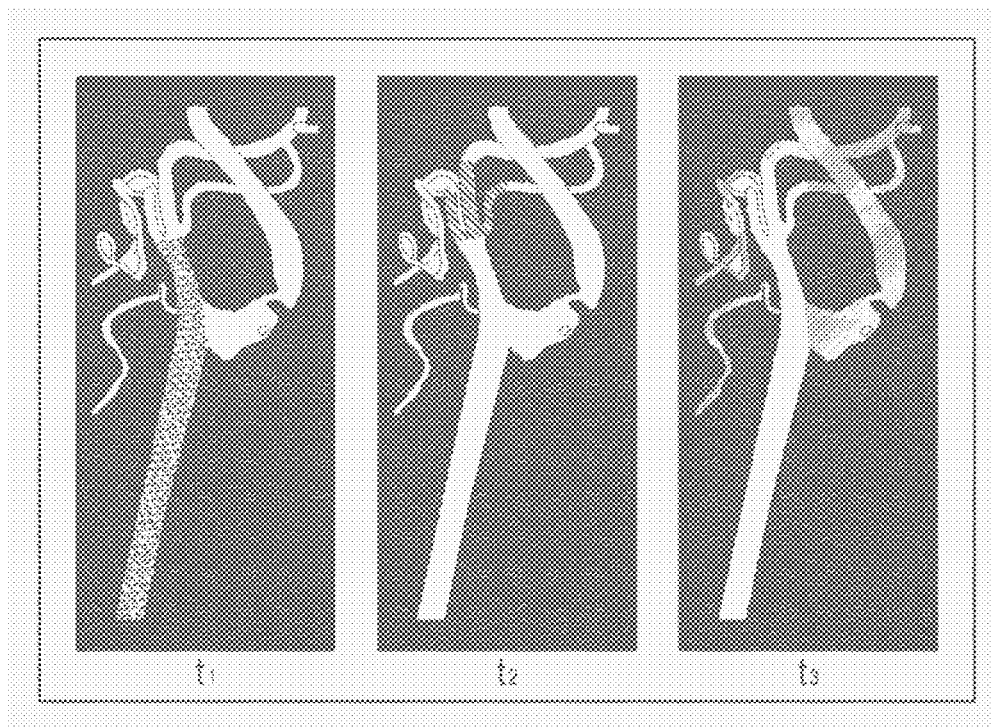
FIG. 14 is a diagram illustrating a screen in which blood vessel X-ray images acquired at each time point are simultaneously displayed and colors of a background area and a blood flow area are differentiated.

In addition, the display unit 172 may differentiate a color of an area in which a blood flow (contrast medium) of the blood vessel X-ray image is positioned and a color of a background area, and display the differentiated colors on the screen. FIG. 14 is a diagram illustrating a screen in which blood vessel X-ray images acquired at each time point are simultaneously displayed and colors of a background area and a blood flow area are differentiated. Through this feature, a user can more clearly recognize the shape of the blood vessels, which may become the basis of accurate diagnosis.

In addition to differentiating the colors, the screen may be displayed in such a manner that a weighted value is given to a shade value of an area in which the blood flow is positioned and a shade value of the background area. In the same manner as in the method of differentiating the colors, the display unit 172 may highlight the blood vessels from the background.

Figure 15:
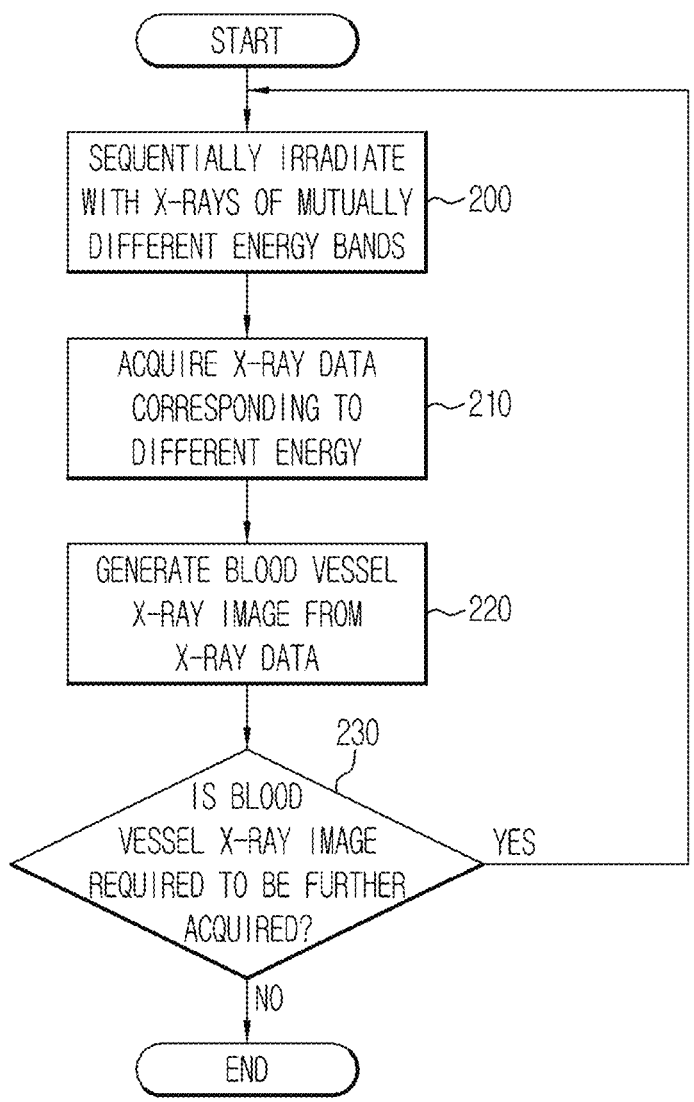
FIG. 15 is a flowchart illustrating an energy subtraction method.

FIG. 15 is a flowchart illustrating an energy subtraction method.

In operation 200, a plurality of X-rays of mutually different energy bands are sequentially radiated to the object 35. The plurality of X-rays of mutually different energy bands may be low energy X-rays and high energy X-rays, but are not limited thereto. Thus, it is sufficient that the plurality of X-rays of mutually different energy bands be radiated.

In operation 210, when the X-rays are irradiated in this manner, X-ray data corresponding to each energy band of the radiated X-rays may be acquired. As shown in FIG. 5, each of the internal materials of the object 35 has a different attenuation coefficient, and the attenuation coefficient of even a single material is changed in accordance with the energy of the irradiated X-rays. Thus, when the X-rays of mutually different energy bands are transmitted through the object 35, the X-ray data may include information about the internal materials of the object 35 corresponding to the mutually different energy bands. Thus, when the X-rays transmitted through the object 35 are detected, the X-ray data for each energy band of the X-rays may be acquired.

In operation 220, the X-ray data corresponding to the mutually different energy bands is acquired, and then blood vessel X-ray images may be generated from the acquired X-ray data.

Specifically, a plurality of pieces of X-ray data is converted into a plurality of X-ray images. For example, when two kinds of X-ray data are acquired by irradiating an object 35 with low energy X-rays and high energy X-rays, the acquired X-ray data may be converted into a low energy X-ray image and a high energy X-ray image.

Next, the blood vessel X-ray images are separated from the converted plurality of X-ray images. In order to separate the blood vessel X-ray images, the blood vessel X-ray images can be separated through an operation of multiplying a weighted value by at least one of the plurality of X-ray images and then performing subtraction. When the low energy X-ray image and the high energy X-ray image are acquired by converting the X-ray data as described above, the blood vessel X-ray images may be separated by a dual energy subtraction method.

However, a method in which the blood vessel X-ray images are separated by multiplying the weighted value by the image and then performing subtraction is merely an example of an image separation method, and thus, the blood vessel X-ray images can be separated using methods other than this method.

In operation 230, whether the blood vessel X-ray image is required to be further acquired is determined. As described above, when the plurality of blood vessel X-ray images are acquired in accordance with a change in the imaging time point, blood flow information such as a blood flow may be confirmed, and diagnosis may be performed according to whether or not there is an abnormality of the blood flow. Thus, whether the blood vessel X-ray image is required to be further acquired is determined, and when it is determined that the blood vessel X-ray image is required to be further acquired, the above-described process may be repeatedly performed.

Figure 16:
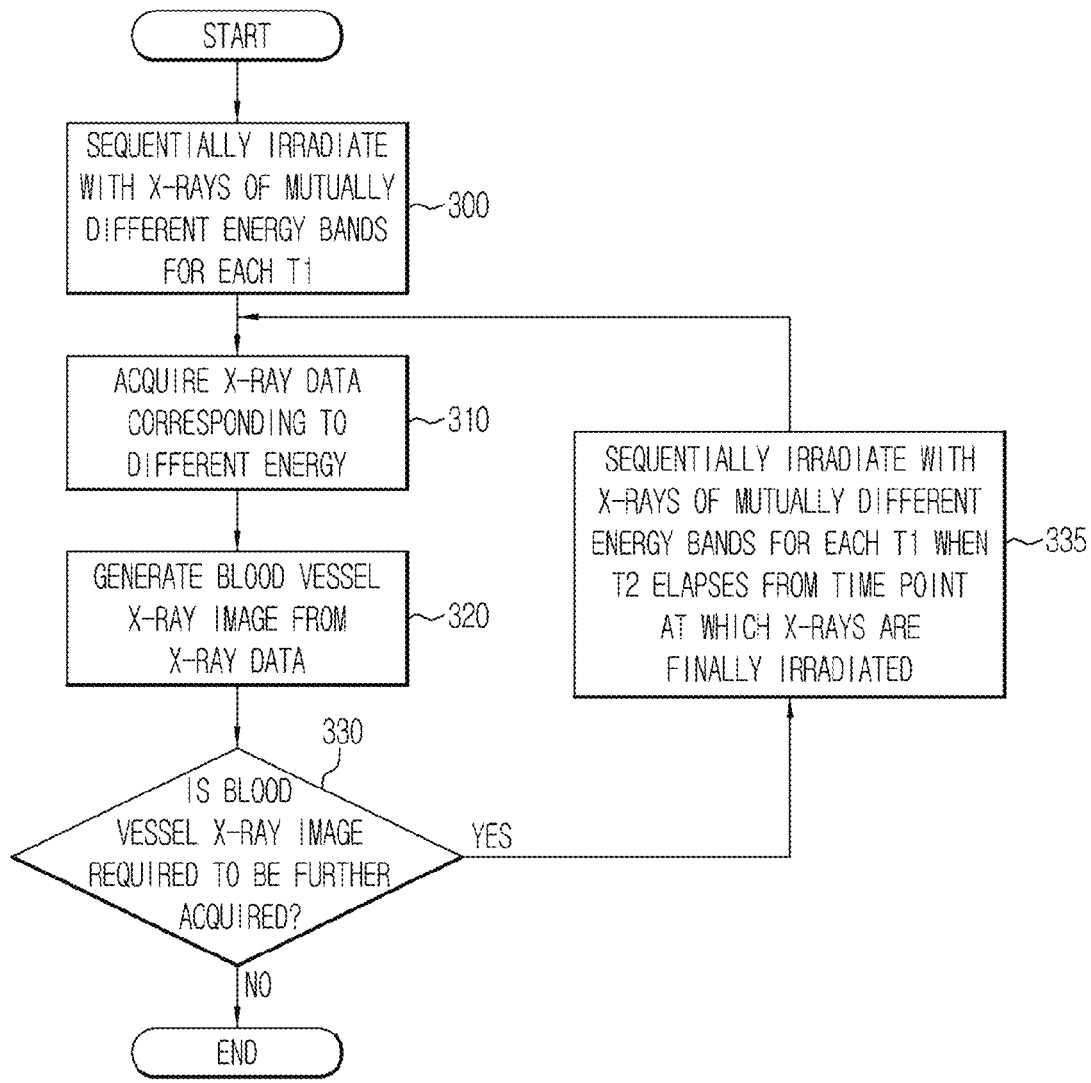
FIG. 16 is a flowchart illustrating an energy subtraction method in which X-rays are non-uniformly irradiated.

FIG. 16 is a flowchart illustrating an energy subtraction method in which X-rays are non-uniformly irradiated.

As described above, as the irradiation interval of the plurality of X-rays which are involved in a single blood vessel X-ray image becomes larger, the probability of occurrence of error due to the movement of the subject 30 and the object 35 is increased. Thus, in order to reduce the irradiation interval of the plurality of X-rays of mutually different energy bands, the X-rays may be non-uniformly irradiated.

In operation 300, a plurality of X-rays of mutually different energy bands are sequentially irradiated to the object 35 for each $T_1$. Here, $T_1$ may be arbitrarily determined by a user or by an internal operation of the X-ray image apparatus. $T_1$ indicates the irradiation interval of the plurality of X-rays of mutually different energy bands, and therefore the probability of occurrence of error due to the movement may be reduced along with a reduction in $T_1$.

The plurality of X-rays of mutually different energy bands may be low energy X-rays and high energy X-rays, but are not limited thereto. Thus, it is sufficient that the plurality of X-rays having mutually different energy bands is irradiated.

Next, X-ray data corresponding to each energy band of the irradiated X-rays is acquired. Since a degree of the X-rays transmitted through the object 35 may vary depending on the mutually different energy bands of the X-ray data, the acquired X-ray data may include information about the internal materials of the object 35.

The same number of pieces of X-ray data as the number of types of radiated X-rays is acquired. For example, when the low energy X-rays and the high energy X-rays are irradiated to the object 35, two kinds of X-ray data may be acquired to correspond to each of the types of X-rays.

In operation 320, after the plurality of pieces of X-ray data are acquired, blood vessel X-ray images may be acquired from the plurality of pieces of X-ray data.

Specifically, first, the plurality of pieces of X-ray data is converted into a plurality of X-ray images. Next, the blood vessel X-ray images are separated from the converted plurality of X-ray images. In order to separate the blood vessel X-ray images, the blood vessel X-ray images can be separated through an operation of multiplying at least one of the plurality of X-ray images by a weighted value and then performing subtraction. However, a method in which the blood vessel X-ray images are separated by multiplying the image by the weighted value and then performing subtraction is merely an example of the image separation method, and therefore the blood vessel X-ray images can be separated through methods other than the above-described method.

In operation 330, whether the blood vessel X-ray image is required to be further acquired is determined. When the plurality of blood vessel X-ray images whose acquisition time points are different from each other are sufficiently acquired, the corresponding process is completed.

When the blood vessel X-ray image is required to be further acquired, the above-described procedure is repeatedly performed. In this instance, in operation 335, when a time $T_2$ elapses from a time point at which the X-rays are finally irradiated, the X-rays of mutually different energy bands are sequentially irradiated again for each $T_1$.

Since the X-rays are required to be non-uniformly irradiated, $T_1$ and $T_2$ may be different from each other. That is, the irradiation interval between the X-rays which are involved in acquisition of the single blood vessel X-ray image is $T_1$, but the irradiation interval between the X-rays which are involved in acquisition of the mutually different blood vessel X-ray images is not necessarily $T_1$.

In particular, $T_1$ may be smaller than $T_2$. As $T_1$ becomes smaller, the error due to the movement of the subject 30 or the object 35 may be reduced. However, $T_2$ is irrelevant to this error and irrelevant to only an acquisition time point of a new blood vessel X-ray image. Thus, when $T_1$ is controlled to be small regardless of $T_2$, the X-rays of mutually different energy bands may be non-uniformly irradiated.

According to the X-ray image apparatus and the control method for the X-ray image apparatus, an error (motion artifact) caused by the movement of the object may be reduced by non-uniformly irradiating the object with a plurality of X-rays of mutually different energy bands, thereby preventing image quality deterioration of the blood vessel image.

Although a few exemplary embodiments have been shown and described, it would be appreciated by those skilled in the art that changes may be made in these exemplary embodiments without departing from the principles and spirit of the exemplary embodiments, the scope of which is defined in the claims and their equivalents.

What is claimed is:

1. An X-ray image apparatus comprising:
   an X-ray generator configured to sequentially irradiate an object with a plurality of X-rays of different energy bands;
   an X-ray detector configured to acquire a plurality of X-ray data corresponding to the plurality of different energy bands by detecting X-rays transmitted through the object;
   a display configured to display at least one blood vessel X-ray image, among blood vessel X-ray images of the object, on a screen, wherein the blood vessel X-ray images are separated from a plurality of X-ray images obtained from the acquired plurality of X-ray data; and
   a controller configured to control operations of the X-ray generator so that the sequentially irradiated plurality of X-rays of the different energy bands are repeatedly irradiated for fixed cycles,
   wherein the X-ray generator is configured to sequentially irradiate the object with the plurality of X-rays for a first time interval in the fixed cycles, and the first time interval is different from a second time interval that is a time interval between a time point at which a final X-ray of a single cycle among the fixed cycles is irradiated and a time point at which a first X-ray of the following cycle among the fixed cycles is irradiated.

2. The X-ray image apparatus according to claim 1, wherein the first time interval is smaller than the second time interval.

3. The X-ray image apparatus according to claim 1, wherein the image processor is configured to correct one of the blood vessel X-ray images with reference to a difference between the plurality of X-ray data corresponding to the same energy band among the plurality of X-ray data acquired in the single cycle, a cycle previous to the single cycle, and a cycle following the single cycle.

4. The X-ray image apparatus according to claim 1, wherein one of the blood vessel X-ray images is acquired from the object into which a contrast medium is injected, and the image processor is configured to correct the one blood vessel X-ray image with reference to a difference between one of the X-ray images obtained by imaging the object before the contrast medium is injected into the object and the one blood vessel X-ray image.

5. The X-ray image apparatus according to claim 1, wherein the display is configured to classify the blood vessel X-ray images in accordance with an acquisition time point and display the classified blood vessel X-ray images on the screen.

6. The X-ray image apparatus according to claim 1, wherein the display is configured to overlap the blood vessel X-ray images and display the overlapped blood vessel X-ray images on the screen.

7. The X-ray image apparatus according to claim 1, wherein the image processor is configured to convert the blood vessel X-ray images into blood vessel X-ray moving images, and the display is configured to display the converted blood vessel X-ray moving images on the screen.

8. The X-ray image apparatus according to claim 1, wherein the display is configured to differentiate colors of a background area and a blood vessel area in the one blood vessel X-ray image, and display the differentiated colors on the screen.

9. A control method for an X-ray image apparatus, the control method comprising:
   sequentially irradiating an object with a plurality of X-rays of mutually different energy bands;
   acquiring a plurality of pieces of X-ray data corresponding to the plurality of mutually different energy bands by detecting X-rays transmitted through the object;
   converting the acquired plurality of pieces of X-ray data into a plurality of X-ray images and separating blood vessel X-ray images of the object from the plurality of X-ray images; and
   controlling the sequentially irradiating of the object to be repeated for fixed cycles,
   wherein the sequentially irradiating of the object includes sequentially irradiating the object with the plurality of X-rays for a first time interval in the fixed cycles, and the first time interval is different from a second time interval that is a time interval between a time point at which a final X-ray of a single cycle among the fixed cycles is irradiated and a time point at which a first X-ray of the following cycle among the fixed cycles is irradiated.

10. The control method according to claim 9, wherein the sequentially irradiating of the object includes controlling the first time interval to be smaller than the second time interval.

11. The control method according to claim 9, wherein the converting of the acquired plurality of pieces of the X-ray data includes correcting one of the blood vessel X-ray images with reference to a difference between the plurality of pieces of X-ray data corresponding to the same energy band among the plurality of pieces of X-ray data acquired in the single cycle, a cycle previous to the single cycle, and a cycle following the single cycle.

12. The control method according to claim 9, wherein one of the blood vessel X-ray images is acquired from the object into which a contrast medium is injected, and the converting of the acquired plurality of pieces of the X-ray data includes correcting the one blood vessel X-ray image with reference to a difference between one of the X-ray images obtained by imaging the object before the contrast medium is injected into the object and the one blood vessel X-ray image.

13. The control method according to claim 9, further comprising:
   displaying one of the blood vessel X-ray images on a screen.

14. The control method according to claim 13, wherein the displaying of one of the blood vessel X-ray images includes classifying the blood vessel X-ray images in accordance with an acquisition time point and displaying the classified blood vessel X-ray images on the screen.

15. The control method according to claim 13, wherein the displaying of one of the blood vessel X-ray images includes overlapping the blood vessel X-ray images and displaying the overlapped blood vessel X-ray images on the screen.

16. The control method according to claim 13, wherein the converting of the acquired plurality of pieces of X-ray data includes converting the blood vessel X-ray images into blood vessel X-ray moving images, and the displaying of the one blood vessel X-ray image includes displaying the converted blood vessel X-ray moving images on the screen.

17. The control method according to claim 13, wherein the displaying of the one blood vessel X-ray image includes differentiating colors of a background area and a blood vessel area in the one blood vessel X-ray image and displaying the differentiated colors on the screen.

* * * * *